(12) United States Patent
Rosnov et al.

(10) Patent No.: US 12,184,415 B2
(45) Date of Patent: Dec. 31, 2024

(54) ROBUST DATA TRANSMITTAL

(71) Applicant: KONINKLIJKE PHILIPS N.V., Eindhoven (NL)

(72) Inventors: Brian Rosnov, Melrose, MA (US); John Price Harrod, IV, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 471 days.

(21) Appl. No.: 16/317,629

(22) PCT Filed: Jul. 25, 2017

(86) PCT No.: PCT/EP2017/068752
§ 371 (c)(1),
(2) Date: Jan. 14, 2019

(87) PCT Pub. No.: WO2018/019825
PCT Pub. Date: Feb. 1, 2018

(65) Prior Publication Data
US 2019/0288796 A1   Sep. 19, 2019

Related U.S. Application Data

(60) Provisional application No. 62/366,316, filed on Jul. 25, 2016.

(51) Int. Cl.
*H04L 1/08* (2006.01)
*H04B 17/318* (2015.01)
(Continued)

(52) U.S. Cl.
CPC .............. *H04L 1/08* (2013.01); *H04B 17/318* (2015.01); *H04L 1/0009* (2013.01); *H04L 1/189* (2013.01);
(Continued)

(58) Field of Classification Search
CPC ..... G06F 1/163; H04B 17/318; H04L 1/0002; H04L 1/0009; H04L 1/08; H04L 1/189; H04W 4/027; H04W 4/029; H04W 80/12
See application file for complete search history.

(56) References Cited

U.S. PATENT DOCUMENTS

| | | | |
|---|---|---|---|
| 5,748,103 A | 5/1998 | Flach et al. | |
| 6,416,471 B1 | 7/2002 | Kumar et al. | |

(Continued)

FOREIGN PATENT DOCUMENTS

| | | | |
|---|---|---|---|
| JP | 10276178 A | 10/1998 | |
| JP | 2007006231 A | 1/2007 | |

(Continued)

OTHER PUBLICATIONS

Ixia, "Best Practices for Eliminating Duplicate Packets", 10 pages (Abstract).

*Primary Examiner* — Jason E Mattis
*Assistant Examiner* — Bao G Nguyen (57) ABSTRACT

Methods and systems for wirelessly transmitting data. Various embodiments determine whether at least one condition is present that affects the ability to wirelessly transmit data. If at least one condition is present, a processor enables a duplicate packet transmittal procedure that transmits at least one previously transmitted data packet.

15 Claims, 6 Drawing Sheets

(51) Int. Cl.
  *H04L 1/00*      (2006.01)
  *H04L 1/1867*    (2023.01)
  *H04W 4/02*      (2018.01)
  *H04W 4/029*     (2018.01)
  *H04W 80/12*     (2009.01)
  *G06F 1/16*      (2006.01)

(52) U.S. Cl.
  CPC ........... *H04W 4/027* (2013.01); *H04W 4/029* (2018.02); *H04W 80/12* (2013.01); *G06F 1/163* (2013.01); *H04L 1/0002* (2013.01)

(56) References Cited

U.S. PATENT DOCUMENTS

| | | | |
|---|---|---|---|
| 6,631,127 | B1 | 10/2003 | Ahmed et al. |
| 9,820,190 | B2 | 11/2017 | Bengtsson |
| 2009/0323579 | A1 | 12/2009 | Bai et al. |
| 2010/0303054 | A1 | 12/2010 | Yang et al. |
| 2011/0085500 | A1* | 4/2011 | Sangiamwong ...... H04L 1/1819 370/328 |
| 2011/0137133 | A1* | 6/2011 | Espina Perez ......... G16H 40/67 600/300 |
| 2012/0029311 | A1 | 2/2012 | Raptis et al. |
| 2012/0263107 | A1 | 10/2012 | Taghavi Nasrabadi et al. |
| 2012/0300663 | A1* | 11/2012 | Lu ........................ H04L 1/1877 370/252 |
| 2013/0014523 | A1 | 6/2013 | Baker |
| 2013/0145236 | A1 | 6/2013 | Baker |
| 2014/0086219 | A1* | 3/2014 | Suzuki ............. H04W 56/0005 370/336 |
| 2014/0369182 | A1* | 12/2014 | De Blasio ............ H04L 1/0009 370/218 |
| 2015/0124711 | A1* | 5/2015 | Krinsky ................ H04L 1/0007 370/329 |
| 2015/0253404 | A1* | 9/2015 | Tomiha .............. G01R 33/3692 324/322 |
| 2015/0381448 | A1* | 12/2015 | Cheng .................... H04W 4/06 370/252 |
| 2016/0089033 | A1* | 3/2016 | Saponas ............. A61B 5/02405 600/483 |
| 2016/0112163 | A1* | 4/2016 | Bai ....................... H04L 5/0057 370/252 |
| 2016/0353327 | A1* | 12/2016 | Larsson .................. H04W 4/02 |
| 2017/0041248 | A1* | 2/2017 | Toy ...................... H04B 10/272 |

FOREIGN PATENT DOCUMENTS

| | | |
|---|---|---|
| JP | 2009088620 A | 4/2009 |
| JP | 2010226625 A | 10/2010 |
| JP | 2011141492 A | 7/2011 |
| JP | 2016105831 A | 6/2016 |
| WO | 2011124996 A1 | 10/2011 |

* cited by examiner

ROBUST DATA TRANSMITTAL

CROSS-REFERENCE TO PRIOR APPLICATIONS

This application is the U.S. National Phase application under 35 U.S.C. § 371 of International Application No. PCT/EP2017/068752, filed on Jul. 25, 2017, which claims the benefit of U.S. Provisional Application No. 62/366,316, filed Jul. 25, 2016. These applications are hereby incorporated by reference herein, for all purposes.

TECHNICAL FIELD

Various embodiments described herein relate to methods and systems for transmitting data and, more particularly but not exclusively, to methods and systems for wirelessly transmitting data notwithstanding connectivity issues.

BACKGROUND

Wireless networks commonly experience connectivity issues that prevent data from being transmitted. These connectivity issues may be caused by, for example, co-channel interference, adjacent channel interference, channel changes, low signal strength, devices that are outside of a coverage area, increases in the signal-to-noise ratio (SNR), dynamic power and channel changes, and off-channel scanning and monitoring, among other issues. Additionally, connectivity issues may arise when a network is initially deployed or when additional components are added to the infrastructure (such as when a new access point is added). In other words, these networks are dynamic and connectivity issues can arise for a variety of reasons.

Patient monitoring devices in health care institutions, for example, are required to work reliably in these environments and use any means necessary to maintain a reliable application-level link. For example, these types of devices may roam to another AP with a better connection. Or, these devices may use more sophisticated application-level support involving extended protocols from both the server side and client side of the system.

One existing technique to ensure data packets are transmitted shall be referred to in this application as "forward error correction" (FEC). FEC accommodates connectivity issues by transmitting redundant data. More specifically, this application-level procedure helps minimize lost data by resending the previously sent packet with a new packet at every send interval.

FEC generally only needs to be implemented on the client side while the server side can use existing packet identification numbers to discard any unnecessary (e.g., redundant) data. However, FEC is not without drawbacks. Specifically, FEC sacrifices network bandwidth by sending the same data packet multiple times. This may impede systems that implement FEC from scaling due to limited RF bandwidth, high network traffic levels, high client densities, or the like.

Another existing technique to ensure data packets are transmitted shall be referred to in this application as "backfilling." Backfilling allows a receiver device to request missing data from a transmitter device that can be lost during roaming and/or when the wireless connection is degraded for any of the reasons mentioned above.

Although wave backfilling helps alleviate some of the disadvantages of FEC, backfilling is also not without its drawbacks. First, backfilling is typically an application-level implementation on both the client and server sides. Second, backfilling can increase the load on the server's resources to manage the transmitting and processing of the backfill requests. Third, wave backfilling requires memory management and sophisticated data management on the client, which may be prohibitive in certain low cost applications.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

According to the foregoing, it would be desirable to provide methods and systems that can reliably transmit data packets notwithstanding connectivity issues that provide reliable data transmission in a scalable manner that utilizes relatively few resources and changes to implementation on the client and server sides.

In one aspect, various embodiments relate to a method of wirelessly transmitting data. The method includes determining, via at least one sensor device, whether at least one condition is present that affects the ability to wirelessly transmit a data packet; and enabling, via a processor, a duplicate packet transmittal procedure that transmits at least one duplicate data packet upon determining the at least one condition is present.

In one embodiment, the method further comprises disabling the duplicate packet transmittal procedure upon determining that at least one condition is not present.

In one embodiment, the duplicate packet transmittal procedure transmits at least one new data packet and at least one previously transmitted data packet.

In one embodiment, the at least one condition includes one or more of a wireless signal's strength below a strength threshold, a number of data packet transmit attempts above a transmit attempt threshold, excessive transmittal retry attempts, and interference between channels on the wireless network.

In one embodiment, the data packet is transmitted from a wearable device worn by a user. In one embodiment, the at least one condition includes one or more of user velocity above a velocity threshold and the wearable device's location with respect to the user.

In one embodiment, the duplicate packet transmittal procedure is implemented on an application layer on a device in a network.

In another aspect, various embodiments relate to a system for wirelessly transmitting data. The system includes at least one sensor device configured to determine whether at least one condition is present that affects the ability to wirelessly transmit a data packet; a memory; and a processor, the processor configured to execute instructions stored on the memory to enable a duplicate packet transmittal procedure that transmits at least one duplicate data packet upon determining the at least one condition is present.

In one embodiment, the processor is further configured to disable the duplicate packet transmittal procedure upon determining the at least one condition is not present.

In one embodiment, the duplicate packet transmittal procedure transmits at least one new data packet and at least one previously transmitted data packet.

In one embodiment, the at least one condition includes one or more of a wireless signal's strength below a strength threshold, a number of data packet transmittal attempts above a transmit attempt threshold, excessive transmittal retry attempts, and interference between channels on the wireless network.

In one embodiment, the data packet is transmitted from a wearable device worn by a user. In one embodiment, the at least one condition includes one or more of user velocity above a velocity threshold and the wearable device's location with respect to the user.

In one embodiment, the duplicate packet transmittal procedure is implemented on an application layer on a device in a network.

In yet another aspect, various embodiments relate to a computer readable medium containing computer-executable instructions for performing a method of wirelessly transmitting data via a wireless network. The computer readable medium includes computer-executable instructions for determining, via at least one sensor device, whether at least one condition is present that affects the ability to wirelessly transmit a data packet; and computer-executable instructions for enabling, via a processor, a duplicate packet transmittal procedure that transmits at least one duplicate packet upon determining the at least one condition is present.

BRIEF DESCRIPTION OF THE DRAWINGS

In order to better understand various example embodiments, reference is made to the accompanying drawings, wherein.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

The methods and systems described herein allow for the wireless transmission of data under conditions that may otherwise inhibit such transmission. One or more sensors detect one or more conditions that typically inhibit the wireless transmission of data. When such conditions are detected, the transmitter may transmit one or more previously sent packets in addition to one or more new packets for transmission, thereby providing the redundant transmission of data when conditions suggest it. In one embodiment, the transmitter sends at least one new packet and at least one packet that was last sent by the transmitter. When the sensors indicate that the condition is no longer present, the transmitter ceases the retransmission of previously-sent packets.

The duplicate packet transmittal procedure is one of many types of mitigation strategies or techniques. For example, other mitigation strategies that may be imitated by the application layer may include roaming, TX power adjustment, frequency scan rate modification, radio communications path modification, backfiling, or the like. Additionally, more aggressive data management techniques can be used depending on the use case. For example, if a patient device is used outside of an ICU, but nonetheless within a healthcare institution (where typical vital sign capture rates are generally between 4-8 hours), techniques such as "store and forward" may be used.

The features described herein may be implemented in a variety of applications, namely, applications in which data is wirelessly transmitted. Patient monitoring devices such as those in healthcare institutions or the like are often required to reliably and/or losslessly communicate patient data wirelessly, such as vital sign information, physiological signals, patient alarm conditions or the like to a caretaker's station (computer, mobile device, tablet, etc.). The caretaker (e.g., nurse, doctor, physician, physician's assistant, or the like) may then analyze the received data to make informed, time critical treatment decisions for the patient. Accordingly, it is critical that patient data is able to reach the caretaker.

Oftentimes, however, wireless networks in environments such as healthcare institutions or the like may be congested with traffic, leading to unsuccessful data transmit attempts. A common scenario is one in which patient data is being transmitted wirelessly over a hospital network. As this data is being transmitted, another person (such as a hospital visitor) may log onto the network and watch an online video. These wireless communications may utilize the same band of frequencies, reducing available bandwidth through collisions, etc. Accordingly, it may be difficult to predict who will be using bandwidth and when, particularly in unlicensed wireless networks which may have a large number of users.

As another example, patients in healthcare institutions are commonly moved to various areas within the healthcare institution. For example, patients may be moved from their rooms to designated areas for various tests and/or medical procedures. As patients are moving throughout the healthcare institution, they are roaming and may be frequently connected to and disconnected from various access points positioned throughout the healthcare institution.

These exemplary scenarios would therefore benefit from the robust and lossless transmission of data. Various features described herein may therefore gather information from various sensor devices to determine whether there could be data loss. If conditions in an environment are such that data loss is likely to occur, a duplicate data packet transmittal procedure may be enabled to transmit duplicate data packets. Therefore, data packets are more likely to be successfully transmitted.

Although the features described herein are largely described in the context of ensuring data transmission for healthcare patients, other applications may benefit from the features as well. For example, any type of product that communicates over a wireless network, sends real-time data, and/or has a high quality of service and/or service level agreement for either regulatory or user experience purposes may benefit from the features described herein.

Figure 1:
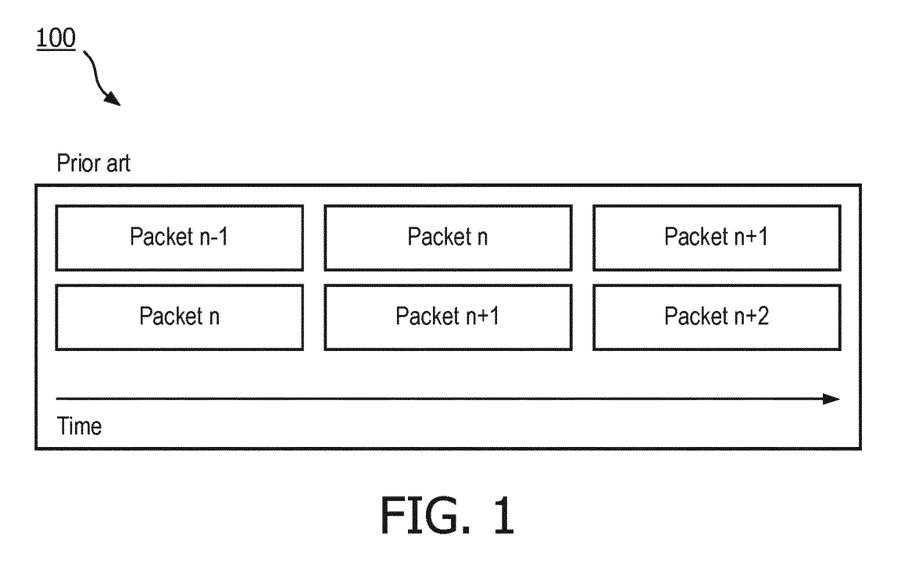
FIG. 1 illustrates an exemplary implementation of a prior art forward error correction (FEC) procedure in accordance with one embodiment.

FIG. 1 depicts an exemplary application of a prior art forward error correction (FEC) procedure 100. As discussed above, the FEC procedure 100 may be implemented to ensure data is transmitted to a receiver device notwithstanding connectivity issues in the wireless network. The FEC procedure 100 may run on the application layer and, at a given send interval, may transmit a current data packet as well as the previously sent data packet. These data packets may comprise, e.g., segments of waveforms measured by biometric instruments, that are transmitted in sequence at predetermined time intervals. If the application-level protocol is tolerant to receiving duplicate packets, this procedure 100 only needs to be implemented on the client-side. As mentioned above, this procedure inevitably requires high levels of bandwidth to constantly send redundant packets.

Various features described herein overcome the disadvantages of FEC and backfilling techniques by monitoring radio statistics and other pertinent environmental variables and only sending duplicate application-level packets when the wireless connection appears to be degraded. Accordingly, various features described herein conserve RF bandwidth by only sending duplicate data packets when necessary.

In addition to conserving bandwidth, various features described herein may, e.g., conserve computational cycles, memory, and battery power of the hardware devices. That is, the devices would use less power as they are not required to send multiple data packets when the wireless signal is acceptable. The devices would also conserve memory by only retaining previously-sent packets when necessary, and computational cycles by transmitting duplicate packets when necessary.

Unlike wave backfilling, but similar to FEC, various features described herein only need to be implemented on the client or server, but not necessarily both components. Various features described herein can, however, be used along with a backfilling procedure based on closed loop feedback in order to maintain a more reliable link between the server and clients.

Figure 2:
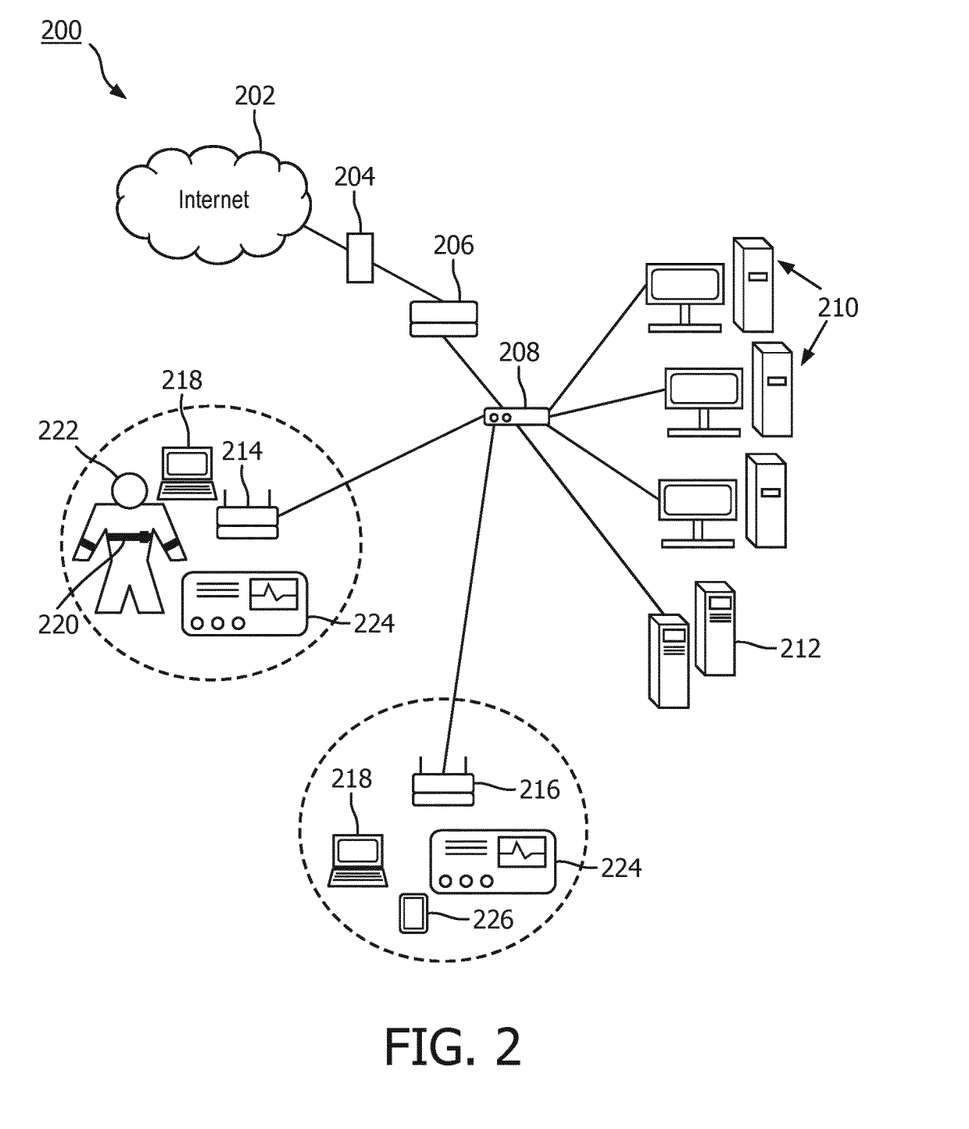
FIG. 2 illustrates a system for wirelessly transmitting data in accordance with one embodiment.

FIG. 2 illustrates a system 200 for wirelessly transmitting data in accordance with one embodiment. Components of the system 200 may be connected to an internet network 202 via at least one modem device 204. The modem device 204 may be in further connection with a router device 206, which in turn may be connected to an Ethernet hub or switch 208. The Ethernet hub 208 may connect a plurality of computers 210 and servers 212 as part of a network (e.g., a hospital network). These computers 210 may be configured as part of a physician's station, for example. The Ethernet hub 208 may also be in operable connection with one or more wireless access points 214 and 216.

The wireless access points 214 and 216 may be located at various positions throughout a building such as a hospital. These wireless access points 214 and 216 may enable connectivity with devices such as laptops 218, sensor devices 220 worn by a patient 222, patient monitoring devices 224, and other types of mobile devices 226. In this particular embodiment, information gathered by sensor devices 220 and/or the patient monitoring devices 224 may be communicated wirelessly to various stations 210 for analysis.

Figure 3:
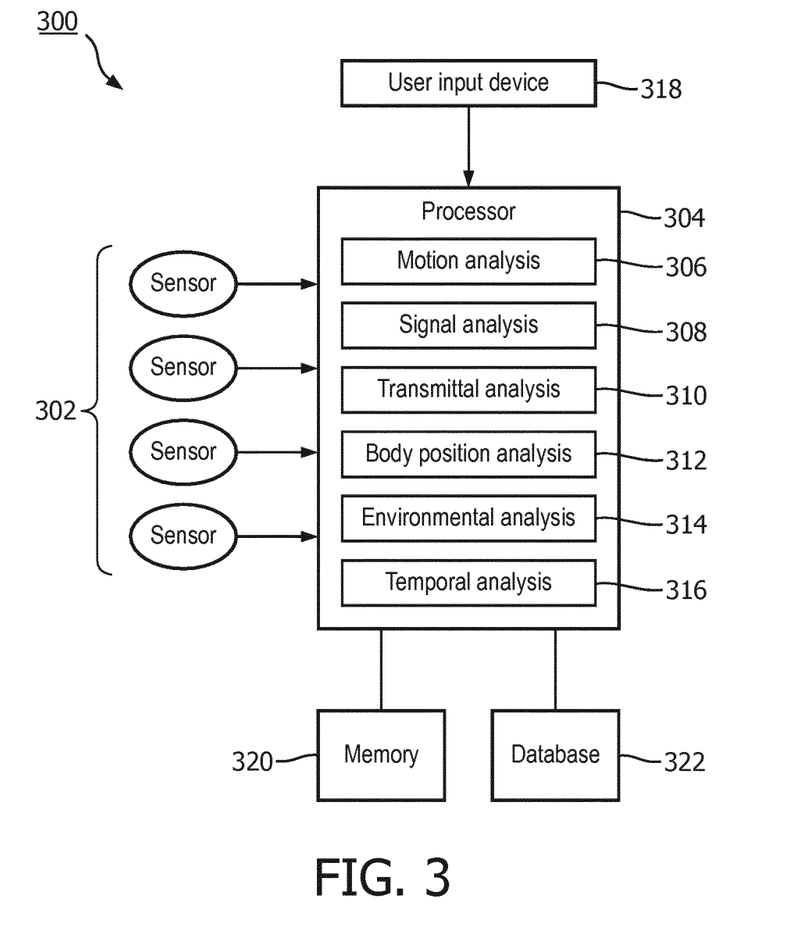
FIG. 3 depicts an apparatus for wirelessly transmitting data in accordance with one embodiment.

FIG. 3 depicts an apparatus 300 for wirelessly transmitting data in accordance with one embodiment. This apparatus may be implemented in one or more components of the system of FIG. 2, such as a sensor device 220, a patient monitoring device 224, etc.

First, one or more sensor devices 302 may gather information related to the wireless network and the wireless network's anticipated ability to transmit data, and/or any physical, environmental, or temporal conditions that may impair wireless communication for the sensor devices 220 and/or patient monitoring devices 224. These sensor devices 302 may be contained in the transmitting device or they may be external to but in communication with the transmitting device.

These sensor devices 302 may include sensor devices configured to gather information regarding a specific user (e.g., a patient) such as an accelerometer operably connected to the user, a gyroscope, a global positioning system (GPS) device, or any other type of device configured to gather information regarding a user that may relate to the network's ability to wirelessly transmit data.

For example, if a user is moving relatively fast as determined by an accelerometer (e.g., on a patient, on a moving gurney or stretcher, etc.), their movement may change the access point that the user's transmitter device is connected to. Changing access points may accordingly affect the network's ability to transmit data.

The user's velocity may be more generally captured by an algorithm that classifies a user's movement. For example, this algorithm may determine, based on the available data, whether a user is sitting, walking, moving in a wheelchair, etc. This classification algorithm may be driven by a series of accelerometers or a three-dimensional accelerometer that provides velocity and context information from a stream of sensor measurements.

As another example, the position of certain transmitter devices with respect to the user's body may affect the transmission of data. For example, the placement of the patient's body (i.e., which is composed mostly of water) between a transmitter and a receiver, known colloquially as "body blocking," is a common issue with radio technology, and the severity can vary based on frequency used, the physical characteristics of the patient, and the location the transmitter device on the patient. Patients commonly wear medical devices which can be particularly susceptible to this effect (e.g., a patient may wear a wireless accelerometer or a multi-parameter telemetry monitor as part of their treatment).

If an accelerometer is monitoring a patient for clinical purposes, the obtained information may also be used to detect when body blocking is likely occurring. For example, if a patient monitoring device is worn on the front of the patient and an accelerometer position algorithm detects that the patient is lying in the prone position (indicating that the device underneath the patient in contact with the bed), then this positioning could affect the ability to transmit data.

Other types of sensor devices 302 may directly measure various characteristics of the wireless connection, such as the wireless signal's strength, the number of data transmittal attempts, etc.

Information gathered by the various sensor devices 302 may be communicated to the processor 304 continuously and in at least substantially real time. This information may be communicated via any suitable wired or wireless connections. The processor 304 may be implemented as part of any of the various devices of FIG. 2 such as the patient monitoring device 224.

The processor 304 may execute various modules to process the information obtained by the sensor devices 302. For example, the processor 304 may include a motion analysis module 306, a signal analysis module 308, a transmittal analysis module 310, a body position analysis module 312, an environmental analysis module 314, a temporal analysis module 316, etc. Each module may receive input data from one or more sensors 302 and process the received data to determine whether one or more conditions are present that may affect the ability to wirelessly transmit data.

For example, the motion analysis module 306 may receive data regarding a user's movement (e.g., the user's acceleration) from an accelerometer. If the motion analysis module 306 determines that the user is moving quickly, the user may be frequently changing access points. This may mean that user devices (such as the wearable sensor devices 220 and/or the patient monitoring device 224) will have difficulty in wirelessly transmitting data.

As another example, the signal analysis module 308 may receive data regarding the wireless signal's strength (e.g., expressed in dBm). The signal analysis module 308 may determine whether a given signal is above or below a certain threshold (which may be defined previously by an operator or which may be determined algorithmically by the device and/or system based on observed factors in the system). A signal with low strength (e.g., below a threshold level of −65 dBm) may mean user devices (such as the wearable sensor devices 220 and/or the patient monitoring device 224) will have difficulty in wirelessly transmitting data.

As yet another example, transmittal analysis module 310 may monitor or otherwise receive information related to the number of data transmittal attempts (or "retries"). That is, if a device has attempted to transmit a given data packet a certain number of times within a predetermined time period (e.g., three attempts within one second), the transmittal analysis module 310 may deduce that there are conditions in the environment that are not conducive to wirelessly transmitting data.

As yet another example, the body position analysis module 312 may monitor or otherwise receive information related to the position and/or orientation of a user. This information may be gathered by sensor devices such as those discussed above. Body-blocking may mean certain user devices (such as the wearable sensor devices 220 and/or the patient monitoring device 224) will have difficulty in wirelessly transmitting data.

As yet another example, the environmental analysis module 314 may detect system level changes in the used frequencies and/or interference conditions amongst "neighborhoods" of various access points that are visible to a sensor device 220 or a patient monitoring device 224. Or, the environmental analysis module 314 may detect any interference between the "community" of various devices visible to a sensor device 220 or a patient monitoring device 224.

As yet another example, the temporal analysis module 316 may detect trends of system level changes amongst the other sensor 302 inputs over time (e.g., periodically or periodically). Additionally or alternatively, the temporal analysis module 316 may detect any unexpected changes and trends in fundamental network timing elements that are critical to the wireless system 200 (e.g., beacon rate timing and variability). This type of temporal analysis may be applied on a device, an access point, an access point neighborhood, and/or on a device community basis, for example.

It is of course noted that not all modules 306, 308, 310, 312, 314, and 316 need to be implemented in a single embodiment, and other types of modules in addition to or in lieu of those shown in FIG. 3 may be used to process various types of data. Additionally, an operator may select or otherwise input which statistics to monitor and for what time period using a user input device 318 such as a mouse, keyboard, touchscreen, etc. For example, not every embodiment or use case will have an accelerometer, so an operator may choose to disable or otherwise not use the motion analysis module 306.

Based on the execution of the various modules 306, 308, 310, 312, 314, and 316 (as well as any other modules) the processor 304 may determine whether the conditions of the environment are acceptable for wirelessly transmitting data. For example, if one or more conditions are present in the environment (such as a signal strength below a certain threshold, user velocity above a certain threshold, and/or body-blocking), the processor 304 may determine that the overall conditions are not acceptable for wirelessly transmitting data.

The output the various modules of the processor 304 may also be weighted based on their severities to determine whether, considering all conditions, data is able to be transmitted. For example, the processor 304 may determine that, even though the user is not moving at all and there is no body-blocking, the overall conditions are not acceptable because of an extremely low signal strength. Similarly, the overall conditions may be acceptable even if there is a moderate level of user movement, but the signal strength is high (e.g., above a certain threshold).

If the overall conditions are not acceptable, then the processor 304 may enable the duplicate packet transmittal procedure (or otherwise keep the duplicate packet transmittal procedure enabled) or may activate or deactivate other possible mitigation strategies. In accordance with various features described herein, the duplicate packet transmittal procedure may operate in accordance with the FEC procedure shown in FIG. 1. That is, each data transmittal attempt may transmit a current data packet as well as one or more previously transmitted data packets, such as the previously transmitted packet.

The processor 304 may also be in communication with a memory 320 and a database 322. Information regarding connectivity issues identified by the processor 304 may be communicated to the database 322 for storage or to some other location for service and troubleshooting purposes. This data can be studied retrospectively to determine if challenging RF conditions, body-blocking, and/or movement could explain a connectivity issue.

Figure 4:
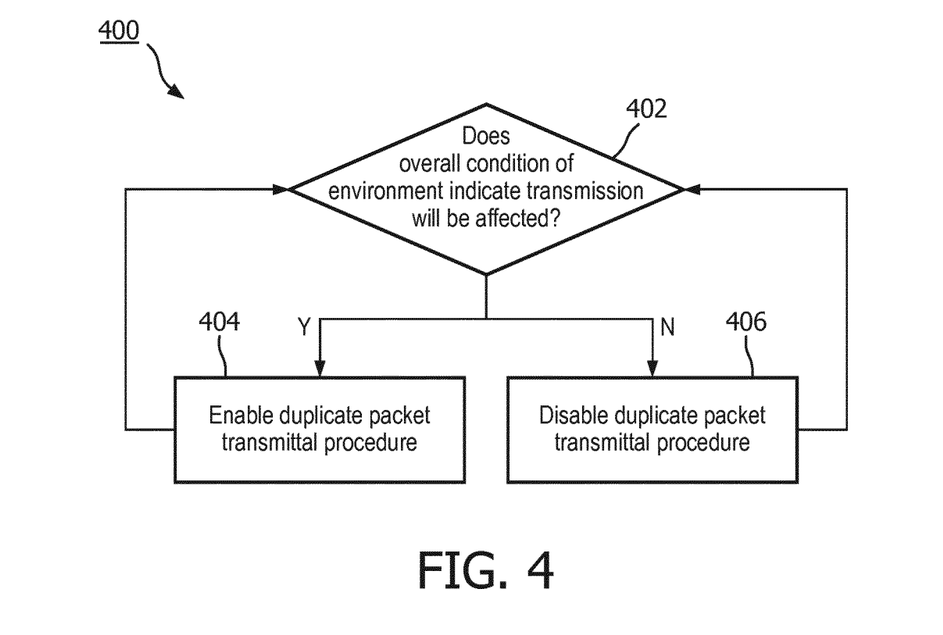
FIG. 4 depicts a flowchart of a method of monitoring a link and enabling/disabling a duplicate packet transmittal procedure in accordance with one embodiment.

FIG. 4 depicts a flowchart of an exemplary method 400 of monitoring a link and enabling/disabling the duplicate packet transmittal procedure. This method 400 may run periodically at set time intervals, use the same types of sensors and processing modules as in FIG. 3, and may be implemented on a patient monitoring device 224, for example.

At predetermined time intervals the processor may determine the overall conditions of the environment including whether at least one condition is present based on the received data (Step 402). If the overall condition of the environment indicates that the transmission of a wireless packet may be affected (e.g., such as the presence of one or more conditions discussed above including, for example, poor network statistics, a quickly moving patient, or a patient oriented in a body position that makes network communication difficult), the processor may enable the duplicate packet transmittal procedure (step 404) or otherwise keep the duplicate packet transmittal procedure enabled (and/or enable/disable any other available mitigation strategy discussed above). This method 400 may then proceed back to step 402 to continuously determine the overall condition of the environment including whether at least one condition is present.

If, on the other hand, the processor determines that the overall condition of the environment does not indicate that transmission will be affected, then the processor may disable the duplicate packet transmittal procedure (Step 406) or otherwise keep the duplicate packet transmittal procedure disabled (and/or enable/disable any other available mitigation strategy discussed above. Accordingly, bandwidth is conserved as duplicate packets are only transmitted when necessary. The method 400 may then proceed back to step 402 to continuously determine the overall condition of the environment including whether at least one condition is present.

More specifically, the method of enabling/disabling the duplicate packet transmittal procedure and transmitting data may be summarized by the pseudocode in Tables 1-3 below. The procedure may begin with an initialization phase in accordance with the following:

TABLE 1

Initialization Phase Pseudocode

If ENABLED:
    SELECT key wireless link statistics to monitor
    SET monitoring_period
    FOREACH statistic, DETERMINE thresholds that ENABLE/
    DISABLE duplicate packet dispatching
    DISABLE duplicate_packet_dispatching The initialization phase may first involve an operator selecting one or more wireless link statistics to monitor (e.g., signal strength, whether the patient is moving, etc.), as well as a time period for monitoring the selected statistic(s). One or more appropriate modules may then analyze each statistic to determine whether conditions are present that suggest the duplicate packet transmittal procedure should be enabled/disabled. Note, in this example, the duplicate dispatching procedure is already be enabled. If there are statistics that suggest data transmittal won't be affected, the duplicate data transmittal (dispatching) procedure may be disabled.

The method may then run a runtime phase that is summarized by the pseudocode in Table 2 below.

TABLE 2

Runtime Phase I (link monitoring)

While application CONNECTED:
    SLEEP monitoring_period
    FOREACH statistic:
        GET current value of statistic
        IF duplicate_packet_dispatching DISABLED:
            IF statistic crosses ENABLE threshold:
                ENABLE duplicate_packet_dispatching
                CLEAR cached_data_buffer
        ELSE IF duplicate_packet_dispatching ENABLED:
            IF statistic RETURNS to acceptable level:
                DISABLE duplicate_packet_dispatching This runtime phase may gather current values for one or more statistics (e.g., signal strength, patient speed, number of transmittal attempts, etc.) and use IF-ELSE statements to determine whether to enable/disable the duplicate packet transmittal procedure. In other words, this phase is largely concerned with monitoring the wireless link. For example, if the duplicate data packet transmittal procedure is disabled (i.e., not active), and one or more statistics crosses an "enable" threshold, then the duplicate packet transmittal procedure may be enabled. Additionally, the method caches data packets so they are sent again on future executions of the algorithm.

On the other hand, if the duplicate packet is enabled and the monitored statistic(s) return to an acceptable level, the duplicate packet transmittal procedure may be disabled. Accordingly, bandwidth is conserved as duplicate packets are sent only when necessary.

The next phase is related to the actual sending of data when the duplicate packet transmittal procedure is enabled. Table 3 below summarizes the pseudocode for this phase.

TABLE 3

Runtime Phase II (data send procedure)

SEND_DATA(current_data_buffer)
    IF duplicate_packet_dispatching ENABLED:
        IF cached_data_buffer AVAILABLE:
            SEND cached_data_buffer
        SEND current_data_buffer
    IF duplicate_packet_dispatching ENABLED:
        cached_data_buffer = current_data_buffer In accordance with the pseudocode of Table 3, if the duplicate packet transmittal procedure is enabled, the procedure may first check there is available cached data (e.g., from one or more previous transmittal attempts). When enabled, the duplicate packet transmittal procedure may transmit both current data as well as any cached data. As data is being gathered over time, there is inherently time passing between sending and resending, and cached data packets are sent on future executions of the algorithm.

Figure 5:
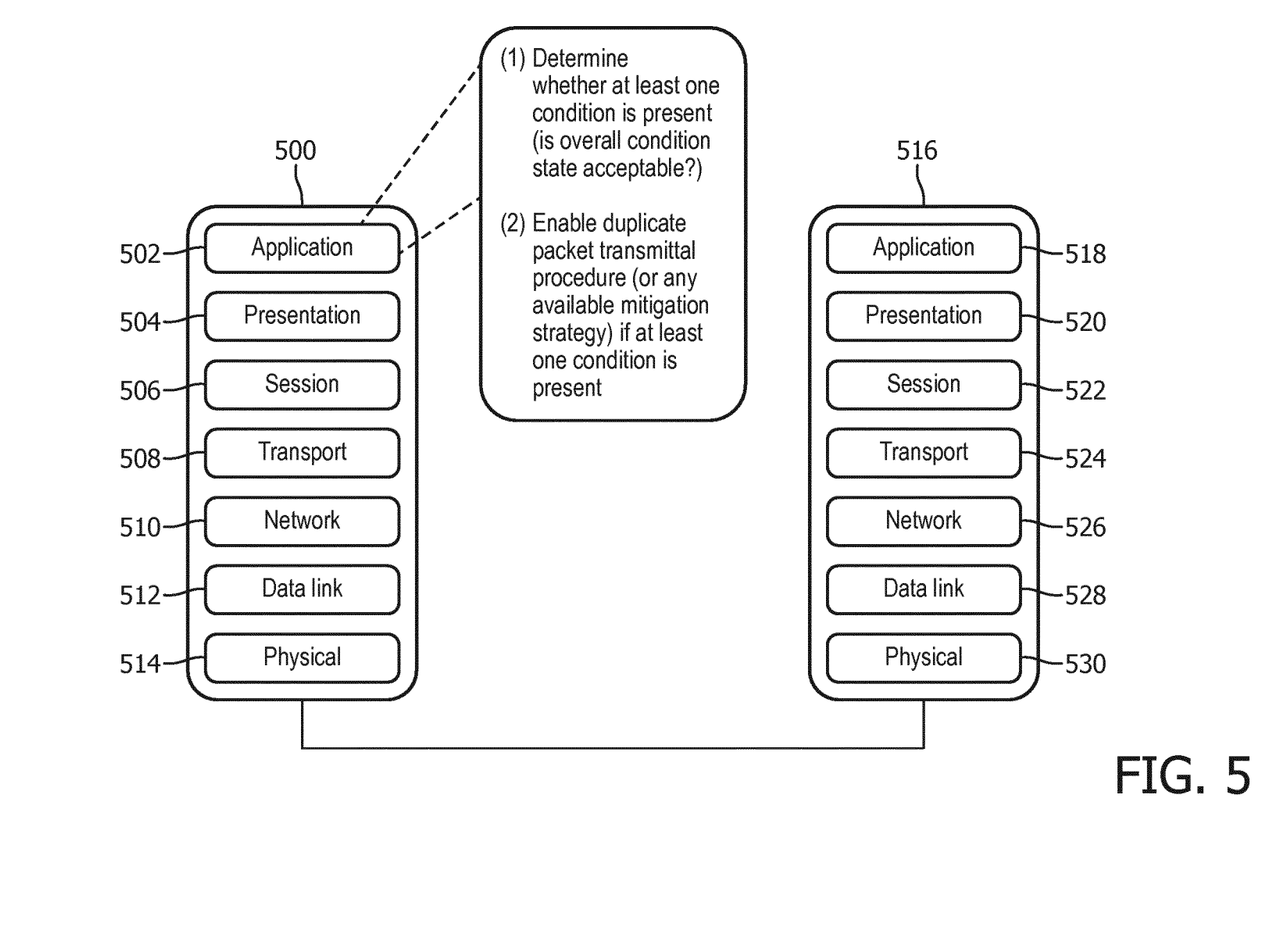
FIG. 5 depicts the implementation of the method of FIG. 4 with respect to the Open Systems Interconnection (OSI) model.

FIG. 5 illustrates the implementation of methods for wirelessly transmitting data such as method 400 with respect to the OSI model. These methods may be implemented on a device 500 such as the patient monitoring device 224 of FIG. 2. This device 500 may, in accord with the OSI model, include an application layer 502, a presentation layer 504, a session layer 506, a transport layer 508, a network layer 510, a data link layer 512, a physical layer 514, and be in communication with another device 516 (also following the OSI model) such as the computer 210 of FIG. 2.

As shown, the steps may be implemented on the application layer 502 of the device 500. Thus, at the application level, the device may duplicate and chunk the data to be transmitted (or vice versa), attach the same sequence number to the duplicate chunks, and pass the chunks down through the lower layers for transmission. Thus, in some embodiments, the lower layers (e.g., the TCP/UDP/IP/MAC/etc. protocol stacks) may not even be made aware of the packet duplication (e.g., while the application sequence numbers may be the same, different TCP sequence numbers may be assigned to the packets carrying the duplicate chunks). On the reception end, the duplicate chunks may therefore pass through the lower layers up to the application layer, where the application layer sequence numbers will be analyzed to determine that one of the chunks may be discarded as duplicate (i.e., in the case where both packets are indeed received at the far end). Additionally, whether or not a particular data packet is received may be acknowledged by the media access control (MAC) layer of the data link layer 528.

Figure 6:
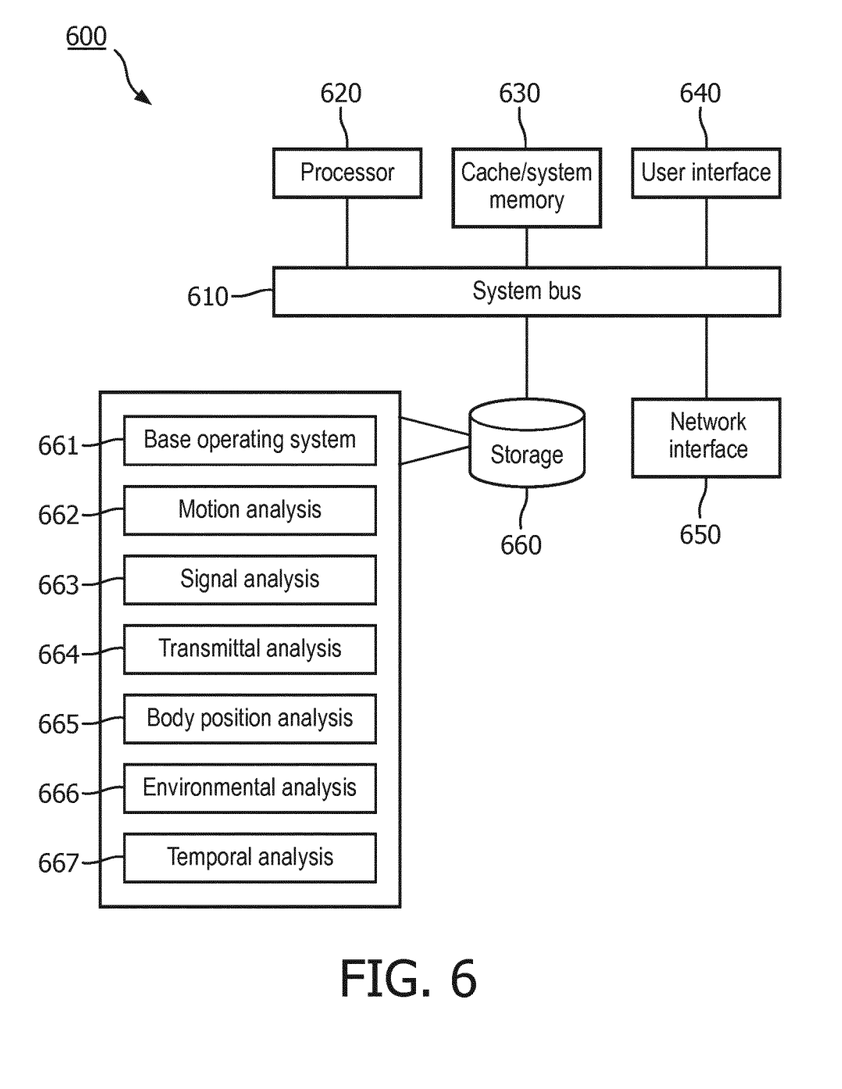
FIG. 6 illustrates an example of a hardware device for implementing the systems and methods described herein in accordance with one embodiment.

FIG. 6 illustrates an exemplary hardware device 600 for wirelessly transmitting data as described herein. The exemplary device 600 may correspond to one or more of the devices of FIGS. 2 and 3, such as, for example, the patient monitoring device 224. As shown, the device 600 includes a processor 620, memory 630, user interface 640, network interface 650, and storage 660 interconnected via one or more system buses 610. It will be understood that FIG. 6 constitutes, in some respects, an abstraction and that the actual organization of the components of the device 600 may be more complex than illustrated.

The processor 620 may be any hardware device capable of executing instructions stored in memory 630 or storage 660 or otherwise capable of processing data. As such, the processor may include a microprocessor, field programmable gate array (FPGA), application-specific integrated circuit (ASIC), or other similar devices.

The memory 630 may include various memories such as, for example L1, L2, or L3 cache or system memory. As such, the memory 630 may include static random access memory (SRAM), dynamic RAM (DRAM), flash memory, read only memory (ROM), or other similar memory devices.

The user interface 640 may include one or more devices for enabling communication with a user. For example, the user interface 640 may include a display, a mouse, and a keyboard for receiving user commands. In some embodiments, the user interface 640 may include a command line interface or graphical user interface that may be presented to a remote terminal via the network interface 650.

The network interface 650 may include one or more devices for enabling communication with other hardware devices. For example, the network interface 650 may include a network interface card (NIC) configured to communicate according to the Ethernet protocol. Additionally, the network interface 650 may implement a TCP/IP stack for communication according to the TCP/IP protocols. Various alternative or additional hardware or configurations for the network interface 650 will be apparent.

The storage 660 may include one or more machine-readable storage media such as read-only memory (ROM), random-access memory (RAM), magnetic disk storage media, optical storage media, flash-memory devices, or similar storage media. In various embodiments, the storage 660 may store instructions for execution by the processor 620 or data upon with the processor 620 may operate. For example, the storage 660 may store a base operating system 661 for controlling various basic operations of the hardware 600.

The storage 660 may also include computer-executable instructions that when executed by the processor 620 provide various modules such as the motion analysis module 662, signal analysis module 663, the transmittal analysis module 664, the body position analysis module 665, the environmental analysis module 666, and the temporal analysis module 667. These various modules may, when executed, process any received data to determine various conditions regarding the environment that may affect the ability to wirelessly transmit data.

It will be apparent that various information described as stored in the storage 660 may be additionally or alternatively stored in the memory 630. In this respect, the memory 630 may also be considered to constitute a "storage device" and the storage 660 may be considered a "memory." Various other arrangements will be apparent. Further, the memory 630 and storage 660 may both be considered to be "non-transitory machine-readable media." As used herein, the term "non-transitory" will be understood to exclude transitory signals but to include all forms of storage, including both volatile and non-volatile memories.

While the device 600 is shown as including one of each described component, the various components may be duplicated in various embodiments. For example, the processor 620 may include multiple microprocessors that are configured to independently execute the methods described herein or are configured to perform steps or subroutines of the methods described herein such that the multiple processors cooperate to achieve the functionality described herein. Further, where the device 600 is implemented in a cloud computing system, the various hardware components may belong to separate physical systems. For example, the processor 620 may include a first processor in a first server and a second processor in a second server.

It should be apparent from the foregoing description that various example embodiments may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles described herein. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention.

The invention claimed is:

1. A method of wirelessly transmitting data from a wearable device worn by a user to a receiver, the method comprising:
   wirelessly transmitting data packets without duplication from the wearable device over a wireless link to receiver;
   gathering information at the wearable device regarding position, orientation and movement of the user relative to the receiver via at least one sensor device;
   determining from the gathered information whether at least one condition is present where a body position of the user impairs an ability to wirelessly transmit the data packets from the wearable device over the wireless link to the receiver, without feedback from the receiver; and
   enabling, via a processor, a duplicate packet transmittal procedure that transmits over the wireless link at least one duplicate data packet of at least one data packet previously transmitted over the wireless link when the at least one condition is present, wherein the at least one duplicate data packet is transmitted from the wearable device worn by the user; and
   disabling the duplicate data packet transmittal procedure when the at least one condition is not present as determined from the gathered information.

2. The method of claim 1, wherein the duplicate data packet transmittal procedure further transmits at least one new data packet over the wireless link in addition to the at least one duplicate data packet.

3. The method of claim 1, further comprising:
   determining whether another condition is present that impairs the ability to wirelessly transmit data packets over the wireless link, wherein the another condition includes one or more of a wireless signal strength below a strength threshold, a number of data packet transmit attempts above a transmit attempt threshold, excessive transmittal retry attempts, and interference between channels on the wireless link.

4. The method of claim 1, wherein the at least one condition includes user velocity above a velocity threshold.

5. The method of claim 1, wherein the duplicate data packet transmittal procedure is implemented on an application layer on a device in a network.

6. The method of claim 1, wherein at least one duplicate data packet is retrieved from a data cache of previously transmitted data packets.

7. The method of claim 1, wherein the at least one condition includes a location of the wearable device with respect to the user.

8. A system for wirelessly transmitting data from a wearable device worn by a user to a receiver, the system comprising:
   at least one sensor configured to gather information regarding position, orientation and movement of the user relative to the receiver;
   a transmitter configured to wirelessly transmit data packets without duplication from the wearable devices over a wireless link to the receiver;
   a memory; and
   a processor configured to execute instructions stored on the memory, causing the processor to:
   determine from the information gathered by the at least one sensor when at least one condition is present in which a body position of the user impairs an ability of the transmitter to wirelessly transmit the data packets from the wearable device to the receiver over the wireless link, without feedback from the receiver,
   enable a duplicate packet transmittal procedure causing the transmitter to wirelessly transmit over the wireless link to the receiver at least one duplicate data packet of at least one data packet previously transmitted over the wireless link when the at least one condition is present, wherein the at least one duplicate data packet is transmitted over the wireless link from the wearable device worn by the user, and
   disable the duplicate packet transmittal procedure causing the transmitter to wirelessly transmit the data packets without duplication over the wireless link to the receiver when the at least one condition is not present as determined from the gathered information.

9. The system of claim 8, wherein the duplicate packet transmittal procedure transmits at least one new data packet over the wireless link in addition to the at least one duplicate data packet.

10. The system of claim 8, wherein the instructions further cause the processor to determine whether another condition is present that impairs the ability to wirelessly transmit data packets over the wireless link, wherein the another condition includes one or more of a signal strength of a wireless signal below a strength threshold, a number of data packet transmittal attempts above a transmit attempt threshold, excessive transmittal retry attempts, and interference between channels on the wireless link.

11. The system of claim 8, wherein the at least one condition includes user velocity above a velocity threshold.

12. The system of claim 8, wherein the duplicate packet transmittal procedure is implemented on an application layer on a device in a network.

13. The system of claim 8, wherein the at least one condition includes a location of the wearable device with respect to the user.

14. A non-transitory computer readable medium storing computer-executable instructions that, when executed by a processor, cause the processor to:
control a transmitter on a wearable device to wirelessly transmit data packets without duplication from the wearable device over a wireless link to a receiver;
gather information regarding position, orientation and movement of a user wearing the wearable device via at least one sensor relative to the receiver;
determine from the gathered information whether at least one condition is present where a body position of the user impairs an ability of the transmitter to wirelessly transmit the data packets from the wearable device over the wireless link from the wearable device to the receiver, without feedback from the receiver;
enable a duplicate packet transmittal procedure causing the transmitter to transmit over the wireless link at least one duplicate data packet of at least one data packet previously transmitted over the wireless link when the at least one condition is present, wherein the at least one duplicate data packet is transmitted from the wearable device worn by the user; and
disable the duplicate packet transmittal procedure causing the transmitter to wirelessly transmit the data packets without duplication over the wireless link to the receiver when the at least one condition event as determined from the gathered information.

15. The computer readable medium of claim 14, wherein the duplicate packet transmittal procedure causes transmission of at least one new data packet over the wireless link in addition to the at least one duplicate data packet.

* * * * *